United States Patent
Lenarz et al.

(10) Patent No.: US 9,192,778 B2
(45) Date of Patent: Nov. 24, 2015

(54) COCHLEA STIMULATOR

(75) Inventors: Thomas Lenarz, Hannover (DE);
Holger Lubatschowski, Hannover (DE);
Guenter Reuter, Hannover (DE);
Gentiana I. Wenzel, Hannover (DE);
Hubert H. Lim, Hannover (DE);
Wolfgang Ertmer, Hannover (DE)

(73) Assignees: MEDIZINISCHE HOCHSCHULE HANNOVER, Hannover (DE);
LEIBNIZ UNIVERSITAT HANNOVER, Hannover (DE)

( * ) Notice: Subject to any disclaimer, the term of this patent is extended or adjusted under 35 U.S.C. 154(b) by 1516 days.

(21) Appl. No.: 12/363,308

(22) Filed: Jan. 30, 2009

(65) Prior Publication Data
US 2010/0198317 A1 Aug. 5, 2010

(51) Int. Cl.
*A61N 5/06* (2006.01)
*A61F 2/04* (2013.01)

(52) U.S. Cl.
CPC ............... *A61N 5/0601* (2013.01); *A61F 2/04* (2013.01); *A61N 5/0622* (2013.01); *A61N 2005/0605* (2013.01)

(58) Field of Classification Search
CPC ............ A61N 1/36032; A61N 1/0541; A61N 2005/0605; A61N 2005/067; A61N 2005/063; A61N 5/0601; A61N 5/0622
USPC .......................................... 607/55–57, 88–89
See application file for complete search history.

(56) References Cited

U.S. PATENT DOCUMENTS 5,305,759 A * 4/1994 Kaneko et al. ................. 600/476
6,671,055 B1 * 12/2003 Wavering et al. ............. 356/478
7,167,741 B2 * 1/2007 Torchia et al. ................. 600/427
7,833,257 B2 * 11/2010 Walsh et al. .................... 607/88
7,883,535 B2 * 2/2011 Cantin et al. .................... 607/89

(Continued)

FOREIGN PATENT DOCUMENTS

WO WO 2005/089497 9/2005
WO WO 2007/013891 2/2007

OTHER PUBLICATIONS

Fridberger; Anders et. al., "Local mechanical stimulation of the hearing organ by laser irradiation", *Auditory and Vestibular Systems, NeuroReport*, vol. 17, No. 1, Jan. 23, 2006.

(Continued)

*Primary Examiner* — Cris L Rodriguez
*Assistant Examiner* — Matthew Nelson
(74) *Attorney, Agent, or Firm* — Greer, Burns & Crain, Ltd.

(57) ABSTRACT

The invention provides a cochlea stimulator for implantation comprising optical fibers of which are coupled to an irradiation source that is controlled by a modulator to generate irradiation specific for a pre-determined range of sound-frequencies. The cochlea stimulator effects a frequency-specific activation of the organ of Corti needed for speech perception especially in noisy environment and more complex sounds. For imparting excitation signals which are generated by modulated pulsed laser irradiation conducted within an optical fiber in order to elicit nervous signals in residual functional organ of Corti sections, the auditory prosthesis preferably contains optical fibers which are dimensioned to terminate in end sections within the cochlea at different sites or sections of the organ of Corti. e.g. having different lengths for locating their end sections at different internal parts of the cochlea.

15 Claims, 6 Drawing Sheets

(56) References Cited

U.S. PATENT DOCUMENTS

| | | | | |
|---|---|---|---|---|
| 8,012,189 | B1* | 9/2011 | Webb et al. | 607/89 |
| 8,333,517 | B2* | 12/2012 | Tanobe et al. | 385/92 |
| 8,396,570 | B2* | 3/2013 | Dadd et al. | 607/137 |
| 2005/0234529 | A1* | 10/2005 | Oghalai et al. | 607/89 |
| 2006/0161227 | A1* | 7/2006 | Walsh et al. | 607/88 |
| 2007/0060983 | A1* | 3/2007 | Merfeld | 607/89 |
| 2010/0074581 | A1* | 3/2010 | Tanobe et al. | 385/93 |

OTHER PUBLICATIONS

Anders Fridberger et al., "Local Mechanical Stimulation of the Hearing Organ by Laser Irradiation", *Auditory and Vestibular Systems*, vol. 17, No. 1, Jan. 23, 2006, pp. 33-37.

Agnella D. Izzo et al., "Laser Stimulation of Auditory Neurons: Effect of Shorter Pulse Duration and Penetration Depth", *Biophysical Journal*, vol. 94, Apr. 2008, pp. 3159-3166.

Agnella D. Izzo et al., "Laser Stimulation of the Auditory Nerve", *Laser in Surgery and Medicine*, vol. 38, 2006, pp. 745-753.

Agnella D. Izzo et al., "Optical Parameter Variability in Laser Nerve Stimulation: A Study of Pulse Duration, Repetition Rate, and Wavelength", *IEEE Transactions on Biomedical Engineering*, vol. 54, No. 6, Jun. 2007, pp. 1108-1114.

Claus-Peter Richter et al., "Optical Stimulation of Auditory Neurons: Effects of Acute and Chronic Deafening", *Hearing Research*, vol. 242, 2008, pp. 42-51.

Gentiana I. Wenzel et al., "Laser-Induced Collagen Remodeling and Deposition within the Basilar Membrane of the Mouse Cochlea", *Journal of Biomedical Optics*, vol. 12, No. 2, Mar./Apr. 2007, pp. 021007-1-021007-7.

Gentiana I. Wenzel et al., "Laser Irradiation of the Guinea Pig Basilar Membrane", *Lasers in Surgery and Medicine*, vol. 35, 2004, pp. 174-180.

\* cited by examiner

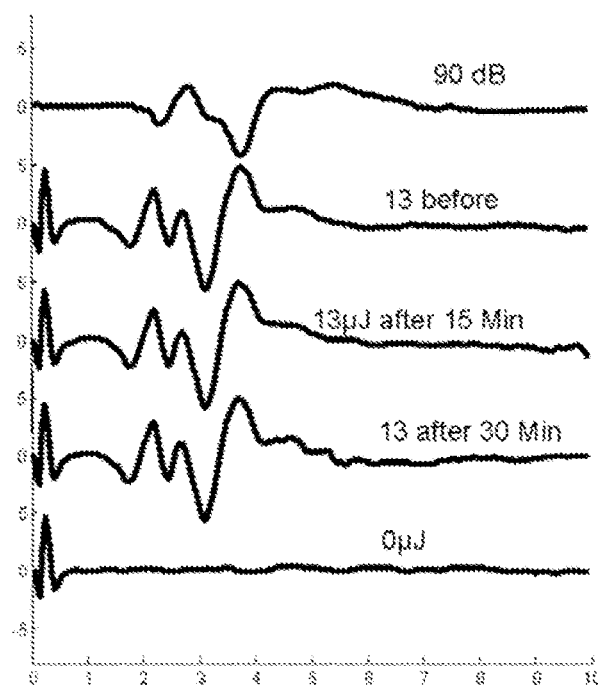

COCHLEA STIMULATOR

FIELD OF THE INVENTION

The invention relates to an auditory prosthesis for permanent implantation, including optical fibres for permanent implantation into the inner ear of a human with impaired hearing, in greater detail, the invention provides an auditory prosthesis which has one or a plurality of optic fibres for the transmission of stimulating light signals for activating the sensory cells within the inner ear. Further, the invention relates to a process for producing the auditory prosthesis of the invention, and to a process for imparting excitation signals to the organ of Corti for eliciting auditory nervous signals in a human or animal.

BACKGROUND OF THE INVENTION

The sensory epithelium of the inner ear is composed of one row of inner hair cells and three rows of outer hair cells, located within the organ of Corti that resides on the basilar membrane. In the intact ear, sound pressure waves from the environment travel through the external auditory canal, are then transmitted through the ear drum and middle ear ossicles to the fluid within the cochlea. The fluid movement within the cochlea induces the depolarization of the sensory epithelium formed by the hair cells. This depolarisation is transformed into nervous signals which are transmitted from the base of the hair cells to the dendrites of the spiral ganglion, which is the first neuron on the auditory pathway and from the spiral ganglion further to the central auditory system, and finally reaching the auditory cortex to elicit a sound perception. Further, it is known that auditory nerve fibres are frequency tuned so that the ones from the base of the cochlea transmit high frequency sound information and the ones from the apical turn are transmit information of low frequency tones to the brain. The nervous signals transmitted via the spiral ganglion cells to the central auditory system can be recorded as auditory brainstem responses (ABR).

STATE OF THE ART

Wenzel et al. in Journal of Biomedical Optics 12(2) 021007 (2007) and WO 2005/089497 A2 describe the manipulation of the hearing impression by modifying the stiffness of the basilar membrane within the inner ear. The basilar membrane is a tuned structure based on its biophysical properties mass stiffness and damping. These again are dependent on the structural molecules collagen, glycosaminoglycans and proteoglycans. The collagen fibres, are regarded as the main source for the stiffness of the basilar membrane Accordingly, changing the structure of the collagen fibres of the basilar membrane would induce changes in the tuning characteristics of the basilar membrane and consequently changes of the cochlear frequency map. i.e. the characteristic frequency of the irradiated sections of the cochlea. The basilar membrane has been stained with trypan blue and irradiated with a 694 nm ruby laser, 3 ms pulses and using a 600 μm core diameter optic fibre. Wenzel et al. demonstrated that laser irradiation of trypan blue stained basilar membrane in vivo induced collagen remodelling within 14 days alter laser irradiation.

Wenzel et al. in Lasers in Surgery and Medicine 35: 174-180 (2004) describe ex vivo experiments demonstrating that collagen changes within the basilar membrane can be induced by laser irradiation of a trypan blue stained basilar membrane. Wenzel et al. discuss that laser irradiation to the cochlea might be used for the therapy of partial hearing loss by changing the frequency responsiveness of the cochlea through collagen remodelling within the basilar membrane. Wenzel et al. indicate that laser treatment of the basilar membrane carries a substantial risk of damaging the neural epithelium by thermal effects of the laser treatment.

The state of art as represented by WO 2005/089497 and Wenzel et al. modifies the frequency response of the basilar membrane by laser treatment of the basilar membrane, resulting in the stiffening of the basilar membrane and hence in a modified frequency map. These publications do not relate to a permanent implant but use a laser for modulating the frequency response behaviour of the cochlea by treatment with a laser. The evocation of auditory nerve signals in response to laser irradiation therefore is not employed.

WO 2007/013891 A2 describes a cochlea implant for placing into the cochlea for stimulating auditory neurons, the implant comprising optical fibres for guiding laser irradiation to a target site of auditory neurons. The auditory neurons which are associated with spiral ganglion cells are stimulated by irradiation with a tunable pulsed laser, thus circumventing signalling by the hair cells of the organ of Corti, i.e. without requiring a functional hair cell.

Fridberger and Ren in NeuroReport, vol. 17, pages 33-37 (2006) quote that laser light can accelerate small objects, and they come to the conclusion that a moderately powerful laser might provide sufficient force to move the organ of Corti. In agreement with their initial considerations that movement of the organ of Corti depends on the power of the laser applied, a 1.3 W laser diode was used at 50 μs pulses separated by 500 ms. Experiments demonstrated that the mechanical response from the basilar membrane was in the form of an oscillating motion which decayed to zero response in approximately 500 μs, which indicates a decline in cochlear sensitivity, damage of the pathway for nervous signal generation and/or of the pathway for nervous signal transduction.

When aiming the laser at bone surrounding the cochlea, no electrical responses were recorded by Fridberger and Ren. Further, repeated exposure of the cochlea to the laser pulse resulted in an abolishment of an evoked response. When aiming the laser at the ossicles of the middle ear, compound action potentials of the auditory nerve could be recorded, which resembled those evoked by acoustic clicks. As identical results were obtained when aiming the laser at the bony bulla, Fridberger and Ren conclude that local heating of the bony structures by absorption of the laser light resulted in a rapid local heating, which in turn generated sound. The results of Fridberger and Ren indicate as well that the hearing organ is locally resonant when this mode of stimulation is used. Further, it was found that repeated exposure caused a decline in cochlear sensitivity, and further resulted in the inability of the cochlea to record additional mechanical responses. They conclude that the organ of Corti can be moved by forces generated by moderately powerful lasers, but with the laser irradiation having the severe limitation in the finding that heating causes cellular damage. From their results, Fridberger and Ren conclude as well that in clinical laser applications, high power lasers used during middle ear surgery for ablating bone surrounding the cochlea may cause hearing loss as the organ of Corti is sensitive to intense light.

Richter et al. in Hearing Research 242, 42-51 (2008) describe that cochlear implants can be used to successfully stimulate the auditory neurons, especially the spiral ganglions, by application of laser irradiation from an optical fibre. In detail, compound activation potentials could be generated by laser stimulation of the spiral ganglion also in deafened experimental animals, which were proven not to have functional sensory cells. As with electrical stimulation by electrodes, the auditory nerves are directly stimulated without participation of sensory cells.

Izzo et al. in Biophysical Journal 3159-3166 (2008) describe the stimulation of the auditory nerves by irradiation at a wavelength of 1.94 μm, differing from the 1.85 μm irradiation used for neural activation to spiral ganglion cells in Izzo et al. in IEEE Transactions on Biomedical Engineering, 1180-1114 (2007).

Further, Izzo et al. in Lasers in Surgery and Medicine 745-753 (2006) showed that it is possible to stimulate the auditory nerve with optical radiation, also in animals in which the hair cells were destroyed through a chronic deafening procedure. Optical stimulation of the auditory nerve could be shown to be stable for several hours without causing obvious damages to the cochlea and radiation energy was elevated to up to 20-40 dB.

The state of art according to WO 2007/013891 and publications of Izzo et al. circumvent the activity of any sensory cells of the ear, e.g. of the organ of Corti, but uses laser pulses for direct stimulation of the auditory nerve. Direct stimulation of the auditory nerve avoids the direct impact of the laser irradiation onto the sensory cells of the organ of Corti, which direct irradiation of the organ of Corti according to Fridberger and Ren causes as a decline in cochlea sensitivity and in an inability to record additional mechanical responses on the basis of their finding that repeated exposure to laser irradiation caused a decline in cochlea sensitivity.

SUMMARY OF THE INVENTION

The invention relates to a hearing aid device for humans or animals with impaired hearing, who have an at least partially functional organ of Corti and a functional nervous signalling pathway from the organ of Corti via the auditory nerve to the brain.

The invention provides for an alternative to the state of art devices which are directly stimulating the auditory nerve as the auditory prostheses or hearing aid device of the invention has one or a plurality of optical fibres for the transduction of stimulating light signals to inner ear sensory cells. Accordingly, the invention is for use in humans having at least some functional hair cells, i.e. at least a fraction of the organ of Corti functional, excluding humans with complete sensorineural deafness. For example, the device of the invention is suitable for implantation into patients with moderate to severe sensorineural hearing loss e.g. praesbiacusis (age related hearing loss), noise induced hearing loss, viral or drug induced hearing loss, and other causes.

In the intact ear, the organ of Corti generates nervous signals in response to mechanical stimuli, which nervous signals are passed to the auditory neurons. The device of the invention contains an arrangement of optical fibres, which optical fibres have a length that is pre-determined for arrangement of their end sections adjacent to the organ of Corti. In detail, the optical fibres are dimensioned to terminate in end sections which are in the very next vicinity but not contacting an impaired but residual functional organ of Corti section. Consequently, the end section of the optical fibres of the device are dimensioned for receiving light irradiation that is modulated in accordance with a sound signal adjacent to an organ of Corti section for transmitting a signal to the pre-determined target sites of residual functional organ of Corti sections. Following implantation, the optical fibres of the auditory prostheses have their end sections localized within the cochlea and adjacent to residual functional organ of Corti sections for delivering an excitation signal that is caused by pulsed light conducted through the optical fibre to an end section. Residual functional sections of the organ of Corti preferably are functional inner hair cells, and optionally excluding outer hair cells. Accordingly, the auditory prosthesis preferably contains optical fibres dimensioned for positioning their end sections into the cochlea and adjacent functional inner hair cells. Therefore, the auditory prosthesis and the method for imparting an excitation signal caused by modulated pulsed laser irradiation conducted to the end section of an optical fibre for stimulation of functional organ of Corti sections are especially suitable for use in humans having no functional outer hair cells but having functional inner hair cells. The excitation signal emitted from the end section of the optical fibre as caused by the pulsed light irradiation conducted to the end section induces the depolarisation of the residual functional inner hair cells generating nervous signals which are then transmitted to the auditory nerve contacting the organ of Corti. Subsequently, the auditory nerve transmits the nervous signals to the brain, where the nervous signals generate a sound perception.

Due to the optical fibres being dimensioned to terminate in end sections adjacent to functional organ of Corti sections, the device of the invention in general is adapted to achieve a localized activation of organ of Corti sections after implantation. As a consequence, and especially in embodiments in which optical fibres of the device are coupled to a laser that is controlled by a modulator to generate irradiation specific for a pre-determined range of sound-frequencies, the device of the invention effects a frequency-specific activation of the organ of Corti, that is needed for speech perception especially in noisy environment and more complex sounds. For imparting excitation signals which are generated by modulated pulsed laser irradiation conducted within an optical fibre in order to elicit nervous signals in residual functional organ of Corti sections, the auditory prosthesis preferably contains optical fibres which are dimensioned to terminate in end sections within the cochlea at different sites or sections of the organ of Corti, e.g. having different lengths for locating their end sections at different internal parts of the cochlea.

The device of the invention is disposed for generating and emitting an excitation signal at the end section of an optical fibre by containing a laser or another pulsed light source, optically coupled to the optical fibre opposite its end section. The excitation signal is generated by the modulated pulsed light irradiation conducted from the light source to the end section of the optical fibre. For the purpose of describing the invention, the term laser also includes irradiation sources producing non-coherent irradiation, e.g. an LED. Depending on the embodiment of the optical fibre end section, the excitation signal can comprise or essentially consist of light irradiation, or in embodiments with an irradiation absorbing material present at the end section of the optical fibre the excitation signal can comprise or essentially consist of vibration. A vibration component of an excitation signal is transmitted to the organ of Corti sections by the device of the invention, e.g. in the process of the invention using the device, by transmission across the intracochlear fluid. Accordingly, the device provides for the generation of excitation signals which can be frequency modulated in dependence on an acoustic signal, and for the transmittance of the excitation signal across the spacing separating the end section of the optical fibre from the organ of Corti section. The spacing of the end section of the optical fibre form the organ of Corti section provides for the absence of mechanical coupling between the optical fibre and the organ of Corti section, as the end section is arranged directly underneath the organ of Corti section, i.e. the optical fibre ends in a spacing from the organ of Corti section without any portions of the device present in the spacing.

In the invention, essentially the only surface of the device emitting energy, e.g. an excitation signal for inducing a nervous signal in an organ of Corti section is the end section of the optical fibre, preferably the cross-sectional surface of the optical fibre, which forms, optionally including an irradiation absorbing material layer, the terminus of the energy conducting path within the device.

The cochlear stimulator device preferably contains a receiver, a transducer of the acoustic signals into electrical current serving as a signal representing the acoustic signal received, a laser or another pulsed light source connected to the transducer for receiving the electrical current and for generating modulated pulsed light irradiation in dependence from the electrical current, and one or more optical fibres optically coupled to the exit of the light source, wherein the optical path for conduction of light irradiation within the device ends in the end section of the optical fibre, which end section is arranged opposite the end to which the light source is coupled to the fibre. For emitting a excitation signal that induces vibration in the organ of Corti section for induction of auditory nervous signals, the device contains an end section terminating each optical fibre, and therefore terminating the optical path within the device in the end section. The optical path contains, and preferably consists of, a laser or another pulsed light source and one or more optical fibres optically coupled to the laser with optical elements like lenses optionally arranged between the laser and the optical fibre and/or at the end of the optical fibre opposite the laser, wherein each optical fibre is dimensioned to terminate in an end section in a spacing adjacent a functional organ of Corti section. The end section is preferably selected from the cross-sectional surface of the end section of an optical fibre, from an optical element like a lens arranged at this cross-sectional surface of the optical fibre, and preferably from the cross-sectional surface of the end section of an optical fibre provided with an irradiation absorbing material.

In the preferred embodiment, the end sections of the optical fibres are provided with a light absorbing material, e.g. contacted by an absorbing material by coating or physical attachment of the absorbing material, because it has been found that an absorbing material contacting the end sections of the optical fibres results in the generation of a mechanical pulse directly at the fibre ending, e.g. in embodiments of the device containing at least 2, preferably 2 to 20, more preferably 5 to 12 optical fibres, each dimensioned to a different length for arrangement adjacent to spaced functional sections of the organ of Corti. The improved spatial resolution of cochlea stimulation obtained by optical fibres having absorbing material at their end sections, and hence the improved resolution of frequency channels, is currently assumed to be the result of the reduction of the scattering or spreading of optical irradiation emitted from the end sections of the optical fibres and/or the result of the generation of vibration caused by laser irradiation due to the presence of the absorbing material.

Generally, in the invention a laser contains a laser medium and an optical resonator arranged at the laser medium as well as optical elements for forming coherent irradiation, i.e. laser irradiation, e.g. one or more lenses.

Preferably, the implantable portion of the device of the invention is designed to have a conformation adapted for insertion or implantation into the cochlea, e.g. the sections optical fibres which are implantable into the cochlea preferably are in an elongate first shape, which can be converted to a second spiral shape during the implantation process into the cochlea. The change of the shape from the first conformation to the second conformation can be caused by a stiffening wire arranged in parallel to the optical fibres and withdrawal of the stiffening wire during the process of implantation. For effecting the change of conformation during the implantation process, the arrangement of implantable sections of optical fibres is elastic and forced by the stiffening wire into a first conformation, while the second spiral conformation, which is the relaxed, i.e. non-stressed conformation, is assumed due to elastic shape recovery by stress-relief at withdrawal of the stiffening wire. In accordance with the optical fibres conducting irradiation to their end sections which are dimensioned for positioning directly opposite and in a spacing to functional sections of the organ of Corti, the implantable portion of the device can also be referred to as an optical cochlea stimulator.

The optical fibres are preferably adapted for implantation of at least a section including their end section into the cochlea for arrangement of the end sections directly in front of functional organ of Corti sections. In the alternative, the fibres are adapted for implantation of at least a section including their end section adjacent the outside the cochlea for arrangement of the end sections adjacent a region of the cochlea opposite one or more functional organ of Corti sections, e.g. with the optical fibres dimensioned for arrangement of their end sections adjacent the basilar membrane.

Preferably, the optical fibres in the invention are essentially parallel to one another, and more preferably, the optical fibres are attached to one another. For attachment of the optical fibres, they can be embedded in a biocompatible, elastic material, e.g. silicone.

Preferably, the optical fibres have a non-transparent radial outer surface, e.g. provided by a non-transparent coating or a non-transparent radial surface structure. The cross-sectional fibre surface, which is preferably perpendicular to the longitudinal axis of the fibre at the end of the fibre which is dimensioned for arrangement adjacent to the organ of Corti, can be optically transparent, but preferably it has reduced transparency or is optically non-transparent to serve as an absorbing material, e.g. a coating by a material of reduced optical transparency or a non-transparent material. This embodiment has been found to predominantly produce mechanical pulses directly at the end section of the fibre. Reduced transparency of a surface of the end section can be obtained by coating with an irradiation absorbing material or by generation of an irradiation absorbing surface structure, e.g. by providing a roughened surface, e.g. by etching or mechanical abrasion.

The end section of the optical fibre preferably has its cross-sectional surface in an angle of 30° to 90°, e.g. at 45° to its longitudinal axis so that the irradiation transmitted along the fibre can exit the end section through the cross-sectional surface or can be reflected by the cross-sectional surface and irradiate in an angle to the longitudinal fibre axis, e.g. between 10° and 120°, preferably at 90° to the longitudinal fibre axis. The angle of irradiation other than along the longitudinal axis of the fibre is preferred for delivery of irradiation to sections of the organ of Corti which are positioned in an angle from the longitudinal axis of the fibre, e.g. for organ of Corti sections parallel to the longitudinal fibre axis it is preferred that the cross-sectional surface of the end section is in an angle of 45° from the fibre longitudinal axis to guide irradiation e.g. at 90° from the fibre axis towards the organ of Corti sections.

It has been found in animal experiments that laser irradiation transmitted through the optical fibres to sections of the organ of Corti elicits auditory brainstem responses (ABR) for laser energy levels from 1-30 µJ/pulse. Prolonged exposure of organ of Corti sections to the pulsed irradiation emitted from the device of the invention did not produce significant cellular damage but resulted in the generation of ABR in accordance with irradiation, and essentially without loss of ABR amplitudes over extended periods of time, indicating that the device of the invention is suitable for long-term use as a cochlear stimulator. From the animal experiments it can be deduced that for activation of the organ of Corti it is preferred that the laser and the optical fibres are set to emit a maximum laser pulse energy in the nJ- to mJ-range, e.g. in a range of about 1 nJ to 1 mJ, preferably in the range of about 1 nJ to 50 µJ, e.g. at a pulse frequency of 1 Hz to 1000 MHz, preferably at 1 Hz to 100 kHz, e.g. at pulse durations in the fs- to ms-range, e.g. in a range of about 1 fs to 1 ms, preferably to 1 µs, preferably in the range of 1 fs to 1 ns or to 1 ns. For optimum signal generation the so-called stress-confinement has to be fulfilled, which means that the laser pulse duration has to be short compared to the time the acoustic signal needs to propagate through the optical penetration depth at the speed of sound:

$$\tau_L \cdot \mu_a \cdot c_0 \ll 1$$

wherein $\tau_L$ is the pulse duration of a single pulse, $\mu_a$ is the optical absorption coefficient of the irradiated material, and $c_0$ is the local speed of sound.

In stress-confinement conditions, essentially no energy dissipation will occur during generation of the acoustic signal.

Due to the spatial confinement of irradiation exiting the end sections of the optical fibres and the dimensioning of the optical fibres for their positioning adjacent pre-determined sections of the organ of Corti, which sections are specific for auditory frequencies, the device of the invention has the advantage of combining frequency-specific excitation of the organ of Corti, and hence of frequency-specific excitation of the auditory nerve contacting the organ of Corti, with a tolerable burden on the organ of Corti sections, i.e. a non-destructive excitation of the sensory cells, allowing for frequency specific cochlear stimulation and for its long-term use. The invention provides for an alternative to the state of art devices which are designed and disposed to directly transmit vibration to the ear by mechanical coupling of a transducer element which emits vibration signals in response to input signals. The cochlear stimulator device of the invention has one or a plurality of light sources (e.g. Q-switched laser, or a light emitting diode (LED) which are coupled to optical fibres for the transduction of stimulating light signals to the end section(s) terminating the optical path, which end sections are dimensioned for arrangement in a spacing and adjacent an organ of Corti section. Due to the dimensioning of the device for positioning of the end section of its optical path in a spaced relationship from an organ of Corti sensory cell, the device of the invention is not designed nor dimensioned for direct transmittance of vibration signals by direct mechanical coupling of the device, e.g. of the fibres to a portion of the natural vibration signal transduction pathway. The spacing of the end section emitting excitations signals effects a stimulation of the sensory cells without mechanical coupling.

In contrast to state of art devices using rigidly mechanically coupled vibration generators to introduce vibration signals to a structure of the ear, the embodiments of the invention surprisingly demonstrate that laser irradiation conducted to the end section of an optical fibre, wherein the optical fibre is dimensioned for arrangement of its end section adjacent and in a spacing from a functional organ of Corti section target site, is sufficient to generate and transmit excitation signals to the target site without direct mechanical coupling of the device to the target site. Whereas state of art devices use a transducer which emits acoustic sound vibration with direct attachment of the transducer to a bony structure of the ear or to the tympanic membrane, the device of the invention contains an optical path essentially consisting of a laser and an optical fibre coupled to the laser, which fibre is dimensioned for arrangement of its end section terminating the optical path adjacent but not contacting the organ of Corti target site. Accordingly, the invention shows that a device having a pulsed light source coupled to an optical fibre, the end section of which is dimensioned for arrangement adjacent a target site, and not in contact with the target site, effects the generation of auditory nervous signals in dependence on frequency modulated pulsed laser irradiation conducted to the end section terminating the optical path.

The device and process of the invention have the advantage over state of art devices which are disposed to transmit vibration signals across a mechanical coupling of a transducer to a target site of the ear in that no direct contact and no direct mechanical coupling of the end section of the optic fibre to the target site is necessary, and should in fact be avoided in order to reduce undesired pulses and other side effects, e.g. infections, the risk of loss of mechanical coupling, the risk of perforation of anatomical structures like the tympanic membrane, the meninges due to mechanical stress caused by the mechanical contact or positioning procedure. Due to the spacing of the end section of the optical fibre from the target site, there is no need for precise placement of a part of the device to a target site, and no need for a mechanical bond between a part of the device and a target site. Accordingly, the device and process of the invention allow for a simple localisation of the end section of the optical fibre adjacent a target site without requirement for mechanical contact, and in addition avoid a change of the vibration characteristics of the target site and of the hearing perception, because no mechanical bond is made, and because no weight is added to the target site, e.g. to an element of the natural vibration transduction pathway.

Without wishing to be bound by theory, it is at present presumed that the excitation of the sensory cells of the organ of Corti effected by laser irradiation exiting from the end sections of optical fibres that are adjacent to the sensory cells is caused by mechanical pulses generated by the irradiated laser pulses, rather than by direct effects of incident irradiation. In embodiments of the invention containing an irradiation absorbing material at the end section of the optical fibre, an excitation signal comprising vibration is assumed to be emitted from the end section, which vibration is generated by laser irradiation conducted from the laser to the end section of an optical fibre. This explanation of the observed gentle and non-destructive excitation over extended periods of excitation of sensory cells by the auditory prostheses of the invention is commensurate with the observation that the provision of the end section of each optical fibre with an absorbing material does not significantly reduce, and preferably increases the excitation of the organ of Corti sections when compared for the same irradiation.

In the practice of the invention, the optical fibres are dimensioned for permanently positioning their end sections adjacent to the organ of Corti sensory cells, and preferably by arrangement of the optical fibres within the cochlea. Accordingly, the optical fibres are preferably dimensioned for permanent positioning their end sections closely adjacent the basilar membrane, because the excitation of organ of Corti sections is effected by laser-light induced excitation signals.

Preferably, optical fibres are of circular cross-section with a core diameter of up to 50 μm, more preferably with a core diameter smaller than 30 μm. The optical fibre can be made out of different materials e.g. from the group of glass, plastics or organic materials, e.g. silk.

The absorbing material, e.g. fixed to the end section of an optical fibre by coating or gluing of the absorbing material, preferably has reduced transparency or is non-transparent to the irradiation. The absorbing material converts incident irradiation that is conducted to the end section of an optical fibre to a mechanical pulse, e.g. a pressure pulse, for exciting the organ of Corti cells. By way of example, absorbing material can be a roughened surface section of the end section of the optical fibre, e.g. obtained by etching, or a metal or metal oxide, e.g. selected from the group consisting of gold, silver, platinum, titanium or oxides thereof, or a natural or synthetic plastic material, e.g. selected from the group consisting of biocompatible polymers Preferably, an irradiation absorbing material is arranged at the cross-sectional surface of the end section of an optical fibre.

For generating laser irradiation in response to input signals, preferably in response to sound, the device in addition to the optical fibres comprises a laser connected to the optical fibres for generation of laser irradiation and coupling the laser irradiation into the optical fibres. Preferably, the laser is coupled and connected to the optical fibres in a distance to the end sections of the optical fibres, e.g. at an end opposite the end sections which are dimensioned for arrangement adjacent to and in a spacing from an organ of Corti section.

The optical fibres can each be coupled with an individual laser, or an optical switch can be arranged between one or more laser media and two or more optical fibres. Embodiments comprising an optical switch preferably have one or more laser media or another pulsed light source coupled to an input side of the optical switch and two or more optical fibres coupled to an output side of the optical switch.

Further, the device optionally comprises an optical modulator for modulating the irradiation, which optical modulator can e.g. be arranged between the laser and an optical fibre, and in the presence of an optical switch, the optical modulator can be arranged between the laser and the input side of the optical switch, or preferably between the output side of the optical switch and an optical fibre.

The laser preferably has an average power output at or below about 100 mW, more preferably of about 1-50 μW, measured at a frequency of 1 Hz. Suitably, the laser emits at a wavelength of 200 nm to 5000 nm, more preferably at a wavelength of 300 nm to 3000 nm, more preferably at 400 nm to 600 nm, most preferably below 550 nm or below 500 nm. The laser emits irradiation with a pulse length in the range of about 1 fs to 1 ms, preferably in the range up to 1 ms, more preferably in the range of 1 ps to 1 ns. An exemplary laser is a 532 nm Nd:YAG laser (obtainable from Quantel Brilliant BW, France), set at 10 ns pulses at a frequency of 10 Hz, e.g. controlled to emit up to 30 μJ/pulse for an average of 500 pulses. Most preferably, especially in embodiments with the end sections of the optical fibres being uncoated, i.e. having no absorption material attached, the device is set to a laser pulse duration shorter than the duration of the transit of an acoustic wave across the irradiated volume. For the limitation of the laser pulse duration to a value smaller than the duration of the transit of an acoustic wave across the irradiated volume, the components of the device preferably are pre-set, e.g. the controller unit controlling the laser, the laser, the optional optical switch, and the optional optical modulator are controlled, e.g. by the controller unit, to limit the laser pulse duration to a preset value. Preferred values for laser pulse duration are in the range of 1 fs-1 msec, preferably 1 ns-1 μsec, more preferably of up to 20 or up to 10 ns, preferably in combination with a maximum pulse energy of 20 μj, more preferably of about up to 13 to 15 μJ.

Preferably, pulsed mode of operation lasers are used, e.g. Q-switched laser, or a light emitting diode (LED)

For controlling the irradiation, the laser is connected to a control unit which activates the light source to emit pulsed irradiation which is modulated in response to frequency signals received by the control unit. The frequency signals preferably are generated in response to sound received by a receiver containing a sound-dependent frequency signal generator. The receiver can be an acoustic receiver or a receiver of radio frequency waves, and the output of the receiver is preferably coupled to the control unit.

The invention also relates to a process for evocation of ABR in a human or in an animal by imparting pulses to the cochlea by the steps of generating pulsed light irradiation in a laser, which pulsed light irradiation preferably is also frequency-modulated in dependency of a sound-signal, transmitting the laser irradiation to a residual functional organ of Corti by one or multiple optical fibre which are dimensioned and arranged with its end section adjacent to a residual functional organ of Corti section. The process can be performed for extended periods of time, allowing the generation of nervous signals in the organ of Corti, and hence the generation of sound perception in the brain of the cochlear stimulator recipient. Process parameters are as described with reference to the device, and preferably, the process is performed by the device as described herein.

BRIEF DESCRIPTION OF THE FIGURES

FIG. 2C shows accumulated auditory brainstem response (ABR) measurement results in hearing animals (90 dB, 13 μJ before), and OBR in the subsequently deafened animals at varying points in time after deafening (13 μJ after 15 min, 13 μJ after 30 min), and a negative test without irradiation (0 μJ)

DETAILED DESCRIPTION OF THE INVENTION AND BEST MODE

The invention is now described in greater detail with reference to the figures and by way of example which describes a best mode for carrying out the invention.

Example 1

Generation of Sound Perception by Pulsed Laser Irradiation of Organ of Corti Cells in an Animal Model 8 pigmented guinea pigs (Charles River Laboratories, Solingen, Germany) of either sex (300 to 600 g) were used according to the guidelines of the Animal Care and Use Committee of the Medical University of Hannover and Lower Saxony. Animals were initially anesthetized with 40 mg/kg of ketamine (Ketanest, Albrecht, Aulendorf/Württemberg, Germany) and 10 mg/kg xylazine (Rompun, Bayer Health Care. Leverkusen, Germany), and maintained with ¼-½ of the initial dosage every 30-60 minutes to maintain an areflexive state. Further administered were 0.05 mg/kg of the anticholinergic agent Robinul (Riemser Arzneimittel, Greifswald-Insel Riems, Germany) intramuscularly, 5 mg/kg of the analgesic Rimadyl (Pfizer, Karlsruhe, Germany) and 13 ml/kg Ringer solution subcutaneously. Throughout the experiment the body temperature was maintained at 38° C. using a water heating pad.

Figure 1:
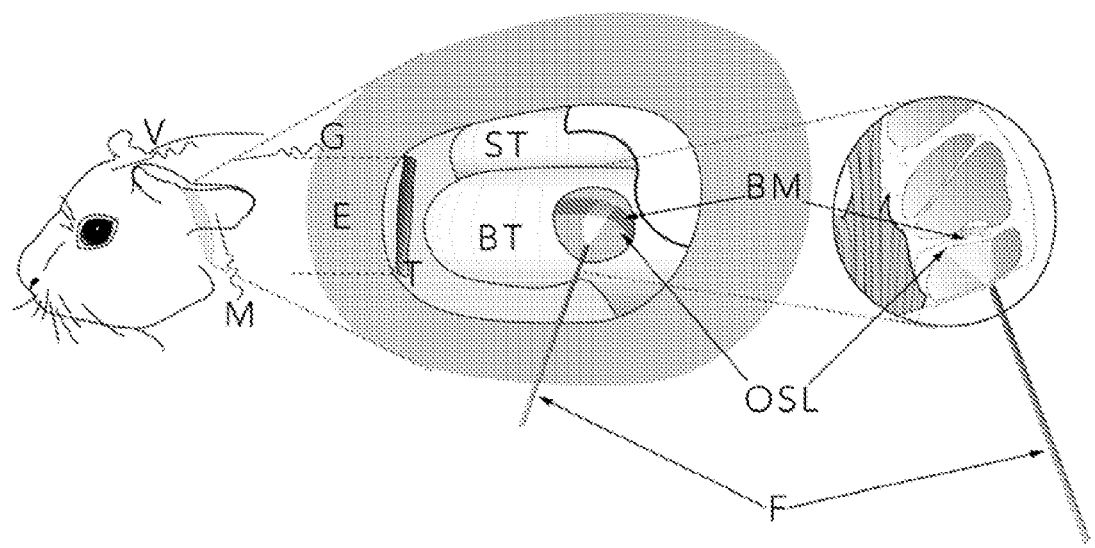
FIG. 1 schematically shows the set up of the example.

For placing the optical fibre with its end section adjacent the organ of Corti, a retroauricular incision was made to expose and open the left tympanic bulla to visualize the round window (RW) membrane. After stabilizing the head with a custom-made holder, a 50-μm core-diameter optical fibre was inserted into the bulla using a micromanipulator (H. Saur, Reutlingen, Germany). The fibre was positioned near the RW membrane and directed towards the basilar membrane (BM) and osseous spiral lamina (OSL) as schematically shown in FIG. 1. In additional experiments, the RW membrane was opened and the fibre was inserted into the cochlea pointing towards the BM and OSL.

For stimulation, a 532 nm Nd:YAG laser (Quantel Brilliant BW, France) was used that delivers 10 ns pulses with a repetition rate of 10 Hz. Optically-induced auditory brainstem responses (O-ABRs) were recorded to varying energy levels (radiant exposure 0-23 μJ/pulse. 500 repetitions/average) and compared them to acoustically-driven auditory brainstem responses (A-ABRs) recorded preoperatively. O-ABRs are shown in FIG. 2B, A-ABRs in FIG. 2A.

The acoustic stimuli were delivered monaurally through polyurethane foam ear tips connected via plastic tubes to calibrated transducers (TIP-300 Tubal Insert Phone, Nicolet Biomedical Inc., Wisconsin, USA.). Since the A-ABRs were initially used to confirm normal hearing thresholds in the animals, varying levels from 10-90 dB SPL in 10 dB steps for clicks (100 μs duration, alternating polarity) were used for stimulation. The contralateral (right) ear was masked with white noise at 30 dB below stimulus level for the left ear. All recordings were obtained in an electrically shielded and sound attenuated chamber using the Nicolet Viking IV® system (Nicolet Biomedical Inc.). Subdermal needle electrodes (Subdermal EMG Needle Electrodes, 12 mm. Medtronic Xomed, Jacksonville. Fla. USA.) were placed at the vertex (reference), right and left mastoids (signals), and in the neck muscles (ground). Each recorded signal was filtered between 300 and 3000 Hz and averaged across 500 trials. The threshold was defined as the lowest stimulus level that generated a visually detectable waveform. For acoustic stimulation, thresholds were considered normal if they were below 40 dB SPL for click stimuli.

For an assessment if OABRs resulted from direct activation of the cochlea or the auditory nerve, deafened guinea pigs were stimulated (i.e., those without functional hair cells). For deafening, a single intraperitoneal injection of 400 mg/kg body weight kanamycin (American Pharmaceutical Partners, Inc., Schaumburg, Ill., USA) was administered followed 2 hours later by an intravenous injection of 25 mg/kg body weight ethacrynic acid (Merck & Co. Inc., Whitehouse Station, N.J., USA). Acoustic thresholds were measured before deafening, one week after the deafening procedure, and immediately before the animals were used for the experiment. The lack of an AABR response at 100 dB sound input was selected as the criterion for a successful deafening procedure. To ensure a functional auditory nerve in these deafened guinea pigs, ABRs caused by electrical stimulation were also obtained. Electrical stimulation was performed with a monopolar ball electrode inserted into the cochlea through the round window and a ground electrode placed into the neck muscle. Single biphasic 50 μs pulses at a rate of 50 pulses/second were applied. The pulse level varied from 25 to 160 μA in 5 μA steps.

Figure 2A:
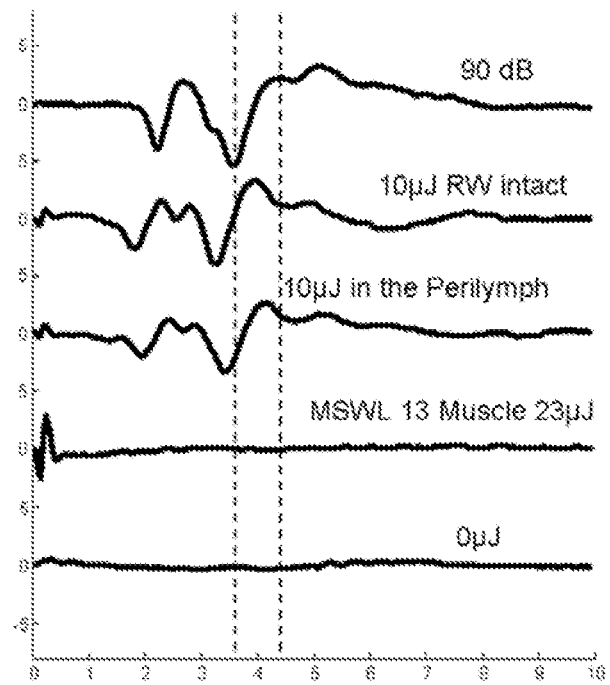
FIG. 2A shows accumulated auditory brainstem response (ABR) measurement results in hearing animals.
Figure 2B:
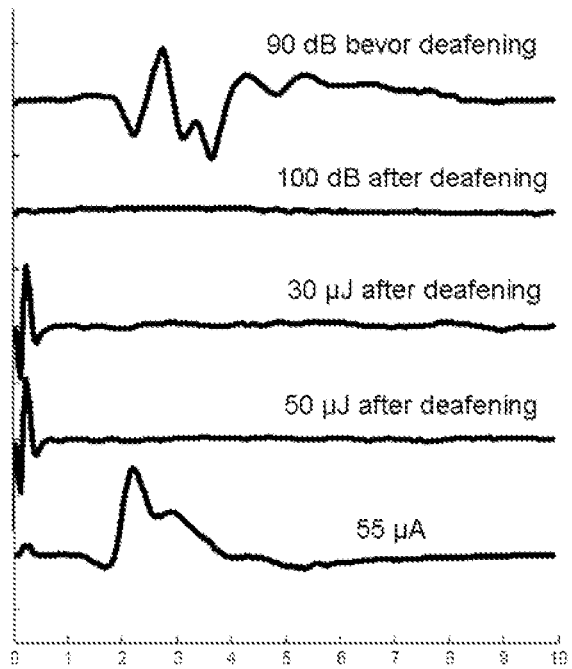
FIG. 2B shows accumulated auditory brainstem response (ABR) measurement results in hearing animals (before deafening), and in the subsequently deafened animals (after deafening)

Results:

Results are shown in FIG. 2A as ABR and OBR, respectively, with the X-axis in ms for hearing animals for 90 dB sound signal applied (90 dB), 10 μJ laser pulses applied at the intact RW, directed onto the organ of Corti (10 μJ RW intact), 10 μJ laser pulses applied into the perilymph and directed toward the basilar membrane through the open round window membrane (10 μJ in the perilymph), laser pulses directed to the soft tissue surrounding the bulla (muscle) indicating no response, and a negative test showing that no irradiation (0 J) didn't induce any nervous signal (control measurement). All O-ABRs exhibited the classical Jewett wave shape obtained from acoustic stimulation except for a shorter latency of about 0.8 μs. The activity was quite similar whether we stimulated through the intact RW or inserted the fibre through the RW demonstrating that the O-ABRs were not dependent on vibration of the RW membrane as shown in FIG. 2A. Since the activity degraded and fluctuated over time after opening the RW, only findings based on stimulation through the intact RW are presented. Further, no O-ABRs were elicited when stimulating the soft tissue (muscle) surrounding the bulla (FIG. 2A) indicating that the activity is not induced by an laser induced artefact in close proximity to the cochlea. Noise generated by laser irradiation hitting structures around the cochlea would have caused a sound that would be transmitted through the ear, was not detected.

For examination of the possible mechanism in which the 532 nm laser elicits brainstem responses, further experiments were performed in deafened guinea pigs that were void of functional hair cells through the administration of ethacrynic acid and kanamycin. When the cochlea was optically stimulated by laser irradiation, no O-ABRs could be excited (FIG. 2C). However, when the cochlea was stimulated with electrical current, it was possible to elicit electrical brainstem responses (EABR, 55 μA). These findings suggest that the green laser light at the parameters used predominantly activates the organ of Corti rather than causing a direct activation of auditory nerve fibres. An activation mechanism due through laser stimulation of the dendrites of the spiral ganglion, e.g. auditory synapses contacting the hair cells, that are not covered by bone instead of the excitation of organ of Corti sections by laser irradiation was practically excluded by the experimental data with deafened animals as therein, no O-ABRs could be evoked by laser irradiation.

FIG. 2B ABR measured in hearing animals (90 dB before deafening) and in deafened animals (100 dB after deafening), as well as OABR in deafened animals (30 μJ alter deafening, 50 μJ after deafening, and 55 μA showing ABR signals evoked by electric stimulation of the cochlea in deafened animals for comparison.

Figure 3:
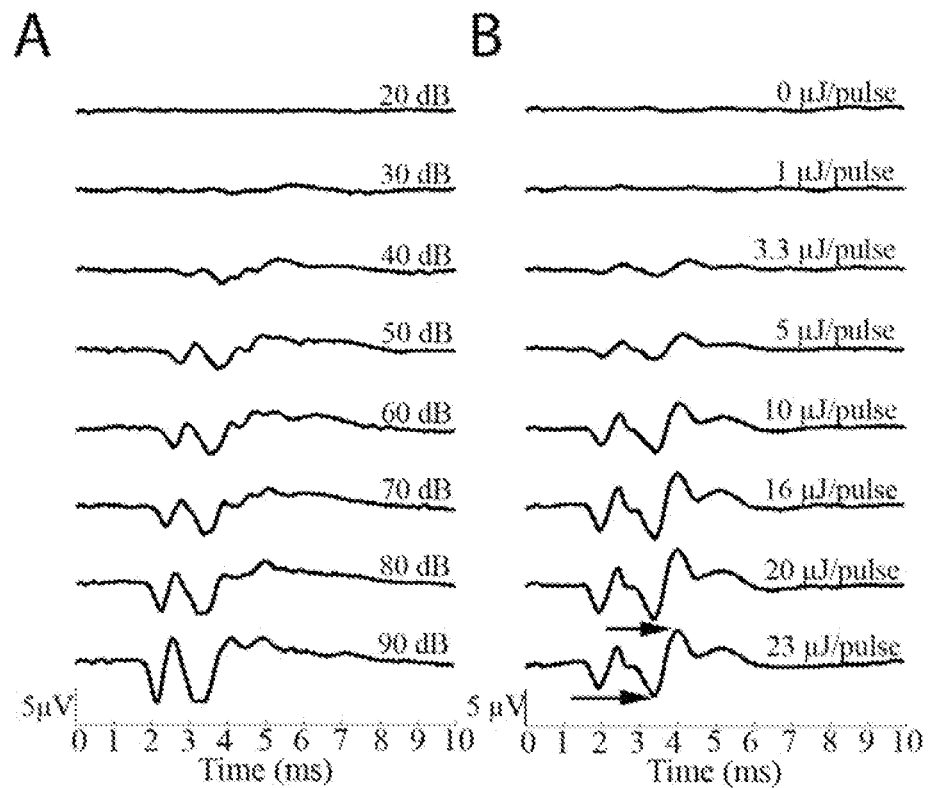
FIG. 3A shows accumulated acoustic auditory brainstem response (AABR) measurement results in hearing animals at various sound levels applied (20 to 90 dB)
FIG. 3B shows accumulated optically induced auditory brainstem response (OABR) measurement results in deafened animals at various laser irradiation energy levels applied (0 to 23 μJ/pulse).
FIG. 3C shows the graph of the magnitude of the OABR measurements in dependence on the laser pulse energy applied.
FIG. 3D shows the frequency specificity of spike activity signals within the inferior colliculus in experimental animals in response to activation of high frequency regions of the organ of Corti sections according to the invention, and FIG. 4 schematically shows an embodiment of the device according invention as partially positioned within the cochlea.

In FIG. 2C, the AABR's in hearing animals (90 dB) are compared with the OABR's in the same hearing animal during continuous optical stimulation with 13 μJ for a period of 30 minutes. The amplitudes of the induced OABR answers remained constant over this stimulation time period indicating no functional damage to the organ of Corti. A similar behaviour of the auditory system in response to acoustic and optical stimulation are represented in FIGS. 3A and B showing increase in amplitude of the evoked ABR's in both types of stimulation.

Figure 3C:
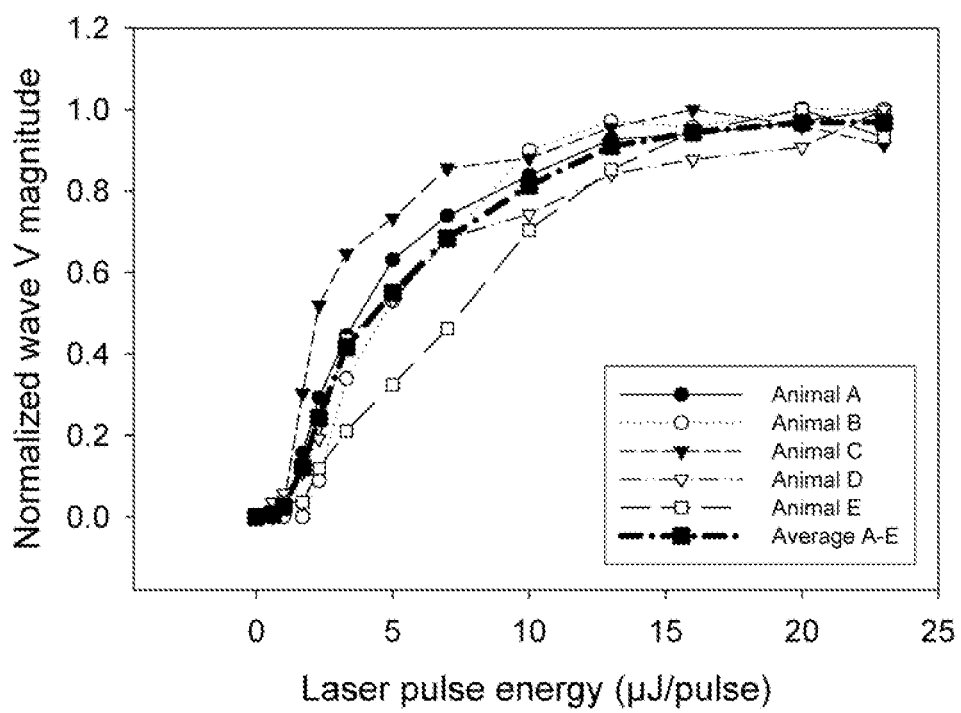

Although the O-ABR peak amplitudes varied slightly across animals, in all cases O-ABR peak amplitudes increased with increasing energy levels generally reaching saturation around 15 μJ (FIG. 3C). The normalized wave V amplitude versus maximum O-ABR peak amplitude values as averaged over the animals and demonstrates similar input/output function and through this demonstrates the consistency of laser stimulation at the RW across animals. The O-ABRs also remained consistent to stimulation over time, including stimulation at 13 μJ/pulse and 10 pulses/s for 30 minutes (FIG. 2B) indicating minimal or no damage within the cochlea due to our repeated laser stimulation. Based on the amplitude values reaching a saturation at approx. 13 μJ pulses, it is preferred that the laser irradiation is pulsed with each pulse having a maximum energy of below 20 μJ to avoid excessive stress on the organ of Corti, while allowing to induce the maximum intensity ABR.

Example 2

Activation of Different Organ of Corti Sections by 532 nm Laser Pulses Causes Frequency Specific Auditory Signals in the Inferior Colliculus Using the general experimental set up as described in Example 1, the frequency specific activity in the inferior colliculus was measured. The multi channel electrode inserted into the inferior colliculus having its contacts along its length, allows for the frequency specific recording of auditory signals in the inferior colliculus, as activity in different regions of the inferior colliculus in response to acoustic signals received by the cochlea. The electrode had 16 segments for measurement and was coupled to a recorder receiving the signals from each of the 16 segments in one of 16 channels. In this example, the optical fibre was coupled to the laser which generated irradiation of 13 μJ/pulse in 10 ns pulses with a repetition rate of 10 Hz at a wavelength of 532 nm.

Figure 3D:
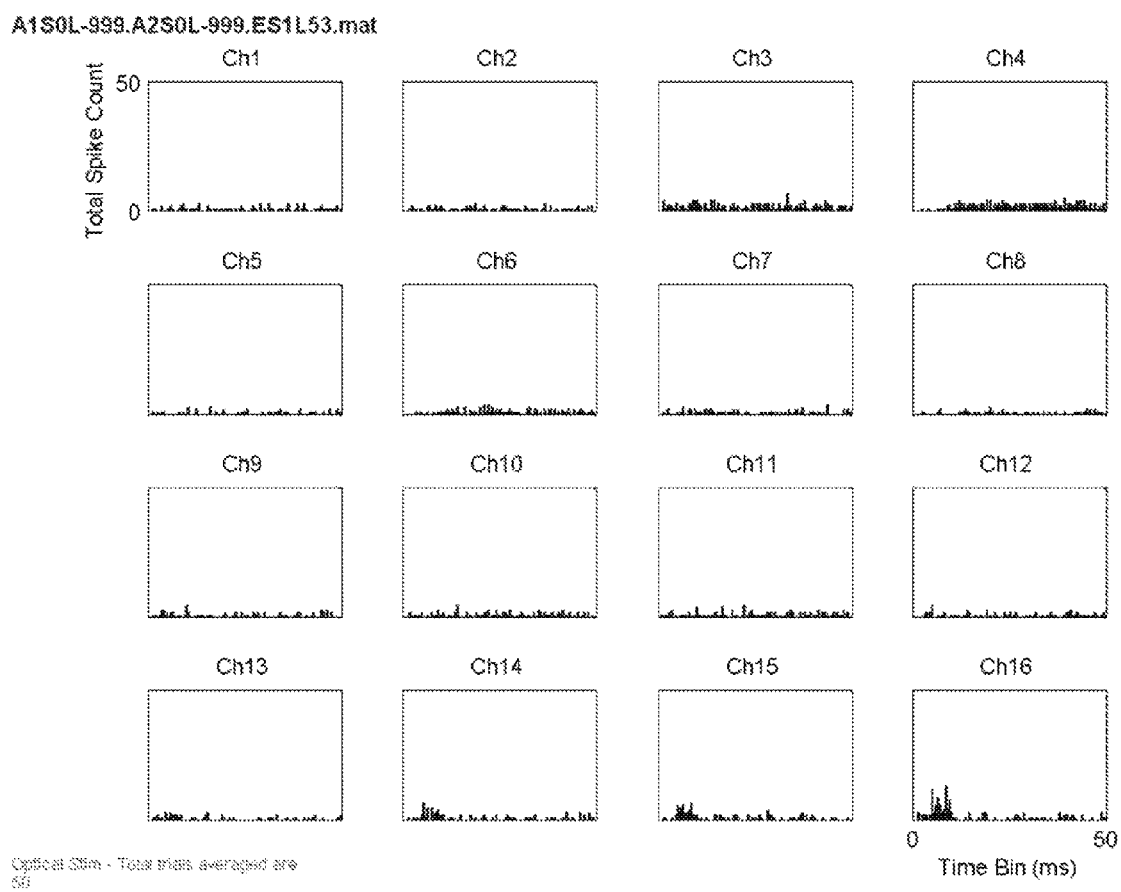

Herein, the optical fibre was inserted into the cochlea at the round window level. The auditory signals measured for the frequency specific layers of the inferior colliculus are shown in FIG. 3D for each channel from channel 1 (Ch1) for the low frequencies represented in the inferior colliculus up to channel 16 (Ch16) for the high frequencies represented in the inferior colliculus. The measurement results show that a signal occurring at about 2 to 10 ms in the high frequency channels 14 to 16 (Ch14 to Ch16) essentially compared to nonspecific background activation level in the lower frequency channels. This result demonstrates that the dimensioning of an optical fibre in the device of the invention for termination in a spacing adjacent an organ of Corti section allows the generation of frequency specific auditory signals in the central auditory pathway.

It can be concluded from these results that the dimensioning of an optical fibre for termination adjacent an organ of Corti section, and hence the conduction of pulsed light irradiation to the organ of Corti section, allows for the generation of auditory signals which are frequency specific. Accordingly, a device of the invention containing two or more optical fibres which are dimensioned to terminate in end sections adjacent spaced apart organ of Corti sections preferred because it is suitable for eliciting auditory signals of a respective number of two or more frequencies.

PREFERRED EMBODIMENT

Figure 4:
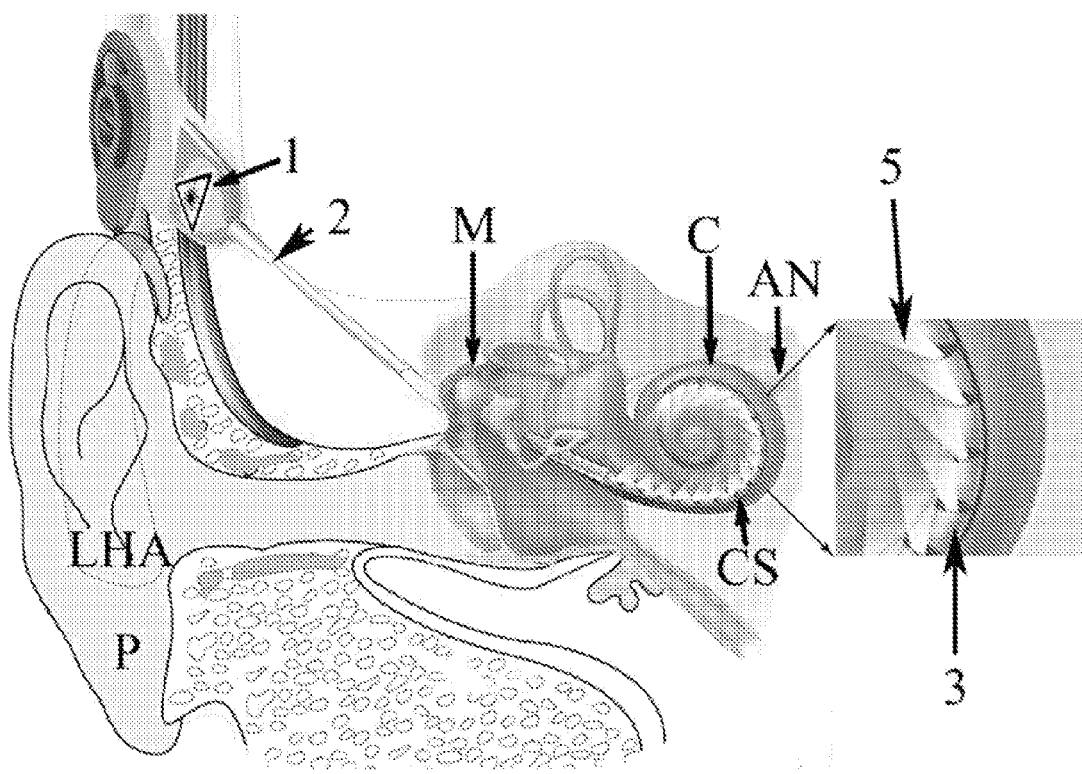

A preferred embodiment of the device is shown schematically in FIG. 4. The device contains a laser 1 and one or more optical fibres 2 optically coupled to the output section of the laser for receiving laser irradiation. As an example for a device containing more than one optical fibres, a bundle CS of optical fibres is shown, each of which is optically coupled to a laser 1. Preferably, in embodiments containing several optical fibres CS, an optical switch is arranged between the laser and the optical fibres for controlling the laser irradiation transmitted to each fibre. Each of the optical fibres 2 terminates in an end section 3, each of which is positioned in a spacing adjacent an organ of Corti section because each optical fibre 2 is dimensioned for termination in an end section 3 in a spacing adjacent an organ of Corti section. Laser irradiation emitted from the laser 1 is conducted along the optical fibres 2 to their end sections 3. At end sections 3, laser irradiation generates an excitation signal, shown in FIG. 4 as a signal cone 5 exiling each end section 3. For eliciting auditory nervous signals in organ of Corti sections in the process of the invention, the optical fibres 2 are positioned to cross the middle ear M to enter the cochlea for arranging the end sections 3 within the cochlea C. The auditory nerve AN delivers nervous signals generated in the cochlea C to the brain.

The laser 1 is coupled to a modulator containing a receiver section, which modulator controls laser 1 to generate pulsed laser irradiation with frequency modulation in dependence on signals received by its receiver section. The signals preferably represent acoustic signals. The modulator preferably is designed for permanent implantation under the skin of a human. The signals can be generated by an external sender that is e.g. part of an external transducer LHA which controls the signals in dependence on acoustic signals. The external transducer LHA can be attached to the pinna P.

The invention claimed is:

1. A process for improving hearing perception in a human with an at least partially functional organ of Corti, the process comprising the steps of:

by producing pulsed light irradiation in a pulsed light source, controlling and modulating the frequency of the light irradiation, transmitting the modulated pulsed light irradiation to partially functional sections of the organ of Corti through at least one optical fibre coupled to the pulsed light source and receiving the pulsed irradiation, wherein the optical fibre is permanently implanted, and which optical fibres are dimensioned and elastically conformal to a spiral shape for termination in end sections in the very next vicinity but not touching functional inner hair cells of the organ of Corti, wherein the cross-sectional surface of the end section of the optical fibre forms an angle of 10° to 80° from the longitudinal fibre axis, and implanting the optical fibre such that an end section of the optical fibre is disposed in the very next vicinity but not contacting functional inner hair cells of the organ of Corti.

2. The process according to claim 1, wherein the pulsed light source is a pulsed laser.

3. The process according to claim 1, wherein the optical fibres are embedded in a biocompatible, elastic material.

4. The process according to claim 1, the biocompatible, elastic material comprises silicone.

5. The process according to claim 1, wherein the end sections of the optical fibres are provided with a light irradiation absorbing material.

6. The process according to claim 5, wherein the absorbing material is selected from the group consisting of surface structure of the fibres, a metal, a metal oxide or a plastic.

7. The process according to claim 1, wherein the cross-sectional surface of the end sections of the optical fibres are arranged in an angle of 45° from the longitudinal fibre axis.

8. A process for improving hearing perception in a human with an at least partially functional organ of Corti, the process comprising the steps of:
   by producing pulsed light irradiation in a pulsed light source,
   controlling and modulating the frequency of the pulsed light irradiation,
   transmitting the modulated pulsed light irradiation to functional sections of the organ of Corti through at least one optical fibre coupled to the pulsed light source and receiving the pulsed irradiation,
   wherein the pulsed light source and the optical fibre form an optical path terminating in an end section of the optical fibre opposite the pulsed light source, wherein the cross-sectional surface of the end section of the optical fibre forms an angle of 10° to 80° from the longitudinal fibre axis, and wherein the optical fibre is implanted with its end section in the very next vicinity to but not contacting functional inner hair cells of the organ of Corti, generating irradiation specific for a pre-determined range of sound frequencies, effecting a frequency-specific activation of the organ of Corti.

9. The process according to claim 8, wherein the pulsed irradiation is a pulsed laser irradiation.

10. The process according to claim 8, wherein the optical fibres are adapted for permanent implantation of at least a section into the cochlea.

11. The process according to claim 8, wherein the optical fibres are adapted for permanent implantation adjacent the outside surface of the cochlea.

12. The process according to claim 8, wherein the very next vicinity is in the range of 0.1 µm to 2 mm.

13. The process according to claim 8, wherein the end sections of the optical fibres are provided with a light irradiation absorbing material.

14. The process according to claim 13, wherein the absorbing material is selected from the group consisting of structure of the fibres, a metal, a metal oxide or a plastic.

15. The process according to claim 8, wherein the cross-sectional surface of the end sections of the optical fibres are arranged in an angle of 45° from the longitudinal fibre axis.

* * * * *